(12) United States Patent
Ozgenc et al.

(10) Patent No.: US 11,583,450 B2
(45) Date of Patent: Feb. 21, 2023

(54) ARRAY OF INDIVIDUALLY PACKAGED ABSORBENT ARTICLES, CONTAINER, AND METHOD OF MAKING

(71) Applicants: ONTEX BVBA, Buggenhout (BE); ONTEX GROUP NV, Erembodegem (BE)

(72) Inventors: Melis Ozgenc, Aalst-Erembodegem (BE); Danny Matthys, Aalst-Erembodegem (BE)

(73) Assignee: Ontex BV, Buggenhout (BE)

( * ) Notice: Subject to any disclaimer, the term of this patent is extended or adjusted under 35 U.S.C. 154(b) by 1089 days.

(21) Appl. No.: 16/314,405

(22) PCT Filed: Apr. 27, 2018

(86) PCT No.: PCT/EP2018/060837
§ 371 (c)(1),
(2) Date: Dec. 29, 2018

(87) PCT Pub. No.: WO2018/202570
PCT Pub. Date: Nov. 8, 2018

(65) Prior Publication Data
US 2019/0151163 A1    May 23, 2019

(30) Foreign Application Priority Data

Sep. 27, 2017  (BE) .................................. 2017/0134

(51) Int. Cl.
*A61F 13/84*    (2006.01)
*A61F 13/15*    (2006.01)
(Continued)

(52) U.S. Cl.
CPC .... *A61F 13/15747* (2013.01); *A61F 13/4704* (2013.01); *A61F 13/5514* (2013.01);
(Continued)

(58) Field of Classification Search
CPC ................ A61F 15/001; A61F 13/5513; A61F 13/5514; A61F 13/55145; A61F 13/4704; A61F 2013/8497
(Continued)

(56) References Cited

U.S. PATENT DOCUMENTS 9,278,035 B2      3/2016  Hashino et al.
2006/0129114 A1*  6/2006  Mason, Jr. ............ A61F 13/472
                                                                604/361
(Continued)

FOREIGN PATENT DOCUMENTS

WO    2004006818 A1    1/2004
WO    2005065605 A1    7/2005
(Continued)

OTHER PUBLICATIONS

International Search Report and Written Opinion for PCT/EP2018/060837; dated Jun. 1, 2018.

*Primary Examiner* — Daniel St Cyr
(74) *Attorney, Agent, or Firm* — Vivicar Law, PLLC

(57) ABSTRACT

A process for making individually wrapped personal hygiene absorbent articles is provided. It comprises: (i) providing a single image with indicia wherein at least one of the indicia is repeated more than once within said single image; (ii) printing a plurality of said single images over a continuous film to form a continuous repetition of the same single image in a side-by-side arrangement; (iii) cutting the printed film and/or web material along a transverse axis such to form a plurality of individual segments of film forming individual wrapping sheets comprising a portion of said single image and sized such to each accommodate one of said personal hygiene absorbent articles therein; (iv) wrapping individual personal hygiene absorbent articles each with one of said wrapping sheets such that a printed portion
(Continued)

of the wrapping sheet is viewable; (v) stacking a plurality of the individually wrapped personal hygiene absorbent articles into a container.

11 Claims, 6 Drawing Sheets

(51) Int. Cl.
*A61F 13/551* (2006.01)
*B41M 3/00* (2006.01)
*B41M 5/00* (2006.01)
*A61F 13/47* (2006.01)

(52) U.S. Cl.
CPC ............... *A61F 13/84* (2013.01); *B41M 3/00* (2013.01); *B41M 5/00* (2013.01); *A61F 2013/15243* (2013.01); *A61F 2013/8497* (2013.01); *B41M 3/008* (2013.01)

(58) Field of Classification Search
USPC ......... 206/440, 438, 457, 459.1, 459.5, 494, 206/812; 156/60
See application file for complete search history.

(56) References Cited

U.S. PATENT DOCUMENTS

| | | | | |
|---|---|---|---|---|
| 2007/0108078 A1* | 5/2007 | Molina | ................... | B65D 75/38 |
| | | | | 206/438 |
| 2007/0267322 A1* | 11/2007 | Kishida | ................... | A61F 13/84 |
| | | | | 206/440 |
| 2008/0077104 A1* | 3/2008 | Baer | ..................... | A61F 13/551 |
| | | | | 604/385.13 |
| 2012/0253308 A1* | 10/2012 | Misiti | ............... | A61F 13/51394 |
| | | | | 604/385.01 |
| 2014/0367290 A1 | 12/2014 | Nomoto et al. | | |

FOREIGN PATENT DOCUMENTS

| | | |
|---|---|---|
| WO | 2006068673 A1 | 6/2006 |
| WO | 2007086034 A1 | 8/2007 |
| WO | 2007135616 A2 | 11/2007 |
| WO | 2009134307 A2 | 11/2009 |

* cited by examiner

ARRAY OF INDIVIDUALLY PACKAGED ABSORBENT ARTICLES, CONTAINER, AND METHOD OF MAKING

CROSS-REFERENCE TO RELATED APPLICATIONS

This application is the national stage application of corresponding international application number PCT/EP2018/060837, filed Apr. 27, 2018, which claims priority to and the benefit of European application no. 17169266.8, filed May 3, 2017 and Belgian application no. BE2017/0134, filed Sep. 27, 2017, all of which are hereby incorporated by reference in their entirety.

TECHNICAL FIELD

The present invention relates to absorbent articles. More particularly, the present invention relates to an individually packaged absorbent article by a wrapper sheet.

BACKGROUND

Absorbent articles such as tampons, sanitary napkins, pantiliners and incontinent pads are devices that are typically worn in the crotch region of an undergarment. More specifically, sanitary napkins and pantiliners, for example, are worn by women in a pair of panties that is normally positioned between the wearer's legs, adjacent to the perineum area. Sanitary napkins and pantiliners are designed to absorb and retain body fluids or discharges (e.g., urine and menses) from the body of women and to prevent body and clothing from soiling. A wide variety of shapes and dimensions of sanitary napkins and pantiliners is currently used by women for the collection of body fluids.

Recent developments for disposable absorbent articles tend to focus on not only improvement of their product functions (e.g., superior absorbency, leakage protection and comfort) but their esthetic features. This trend is particularly true for sanitary napkins and baby diapers. Such disposable absorbent articles are disclosed in, for example, WO 2004/006818.

The esthetic designs are typically implemented by printing graphics at one (or more) of component members of those disposable absorbent articles (e.g., a backsheet). This means that such esthetic features have been becoming one of important product features in recent disposable absorbent articles. It is believed that such esthetic features can provide emotional benefit to users, and thus can decrease users' melancholic mood during the menstruation period. So, there is an intention of showing the esthetic features of disposable absorbent articles.

In recent disposable absorbent articles (typically sanitary napkins and pantiliners), however, each pad is folded and wrapped individually by a wrapper sheet. The materials of such wrapper members are typically polyethylene films or sometimes nonwoven materials which are mostly non-transparent. This is because consumers of those disposable absorbent articles do not want other people to notice or show they are carrying such a pad(s). Also, after the soiled pad is wrapped by the wrapper sheet for disposal, such the non-transparent package member can prevent the soiled pad from being seen through the wrapper sheet. These needs are contrary to the intention of showing the esthetic features of disposable absorbent articles.

Developments have been made towards individually packaged absorbent articles that can show an aesthetic feature of the absorbent article through a wrapper sheet while controlling the visibility of the soiled absorbent article seen through the wrapper sheet after use, such as described in EP1978905A1.

In other alternative developments, focus has been on providing individually wrapped absorbent article that is wrapped in a wrapping sheet wherein the wrapping sheet has a colored part on the inner surface on the side of the absorbent article, and the colored part of the wrapping sheet can be seen from the outside of the individually wrapped product but the absorbent article cannot be seen from the outside of the individually wrapped product, such as described in U.S. Pat. No. 9,278,035B2.

US2014/0367290A1 provides individually wrapped absorbent articles, wherein each article is wrapped within a pouch with printed indicia thereon. The printing shows solid demarcation lines present throughout the image at least separating each designated section for wrapping each absorbent article. The process for manufacturing such absorbent article package requires a registered cutting step.

WO2006/068673A1 and WO2005/065605 also disclose individually wrapped absorbent articles, wherein each article is wrapped within a pouch with indicia thereon.

Nevertheless, there is still need for individually wrapped absorbent articles that are directed to extending the user experience not only during use, but also before and after use. Moreover, there is a need to provide an effective means for users to identify themselves with the product and improve the sensory journey on what otherwise remains a mundane and daily use product. And finally, there is a need to provide also a cheap and effective process that allows such product differentiation to be achieved.

SUMMARY OF THE INVENTION

In a first aspect, the present disclosure relates to a process for making individually wrapped personal hygiene absorbent articles comprising the steps of: (i) providing a single image having a width and a length and comprising one or more, preferably a plurality of, indicia wherein at least one of the indicia is repeated more than once within said single image; (ii) printing said single image, preferably a plurality of said single images, over a continuous film and/or web of material typically to form a continuous repetition of the same single image in a side-by-side arrangement with the length of the image extending along a length of the continuous film and/or web of material and the width of the image corresponding to the width of said continuous film and/or web of material; (iii) cutting the printed film and/or web material along a transverse axis perpendicular to said length such to form a plurality of individual segments of film and/or web material forming individual wrapping sheets comprising a portion of said single image and sized such to each accommodate one of said personal hygiene absorbent articles therein, preferably wherein each of said plurality of individual segments comprise at least one said indicia; (iv) wrapping individual personal hygiene absorbent articles each with one of said wrapping sheets such that a printed portion of the wrapping sheet is viewable; (v) stacking a plurality of the individually wrapped personal hygiene absorbent articles into a container; wherein said image is free of demarcation lines extending perpendicular to the length and parallel to the width of said image, and wherein said stacked plurality of individually wrapped personal hygiene absorbent articles when unwrapped and/or positioned side by side substantially reconstruct said single image, and wherein the cutting step is not registered.

In a further aspect, the present disclosure relates to a container comprising a plurality of individually wrapped personal hygiene absorbent articles, wherein each personal hygiene absorbent article is wrapped within a pouch formed by a printed wrapping sheet, each pouch comprising an interior surface facing the personal hygiene absorbent article and an external surface opposite thereto, the external surface comprising printed indicia thereon, and arranged such that when a plurality of said pouches within the container are stacked side-by-side they form at least one single substantially harmonious image, and wherein at least a portion of said pouches are viewable through said container.

In a further aspect, the present disclosure relates to an array of pouches comprising a wrapping sheet each for containing a single personal hygiene absorbent article therein, each said pouch comprising an interior surface facing the personal hygiene absorbent article and an external surface opposite thereto, the external surface of each said pouches comprising printed indicia and arranged such that when a plurality of said pouches within said array are stacked side-by-side they form at least one single substantially harmonious image.

In a preferred aspect of the present disclosure, the plurality of indicia of the image are skewed along an axis parallel to the width (W), preferably wherein each indicia has a centerline and each said centerline being separated by a distance (d1, d2) along said axis. In an embodiment each distance (d1, d2) is substantially equal, in an alternative embodiment each distance (d1, d2) is different.

In a preferred aspect of the preset disclosure, the distance (d1, d2) is greater or equal to a second distance separating a cutting and a sealing station and/or wherein the distance (d1, d2) is from 90 mm to 150 mm, preferably from 95 mm to 140 mm, more preferably from 110 mm to 130 mm.

DETAILED DESCRIPTION OF THE INVENTION

Figure 1:
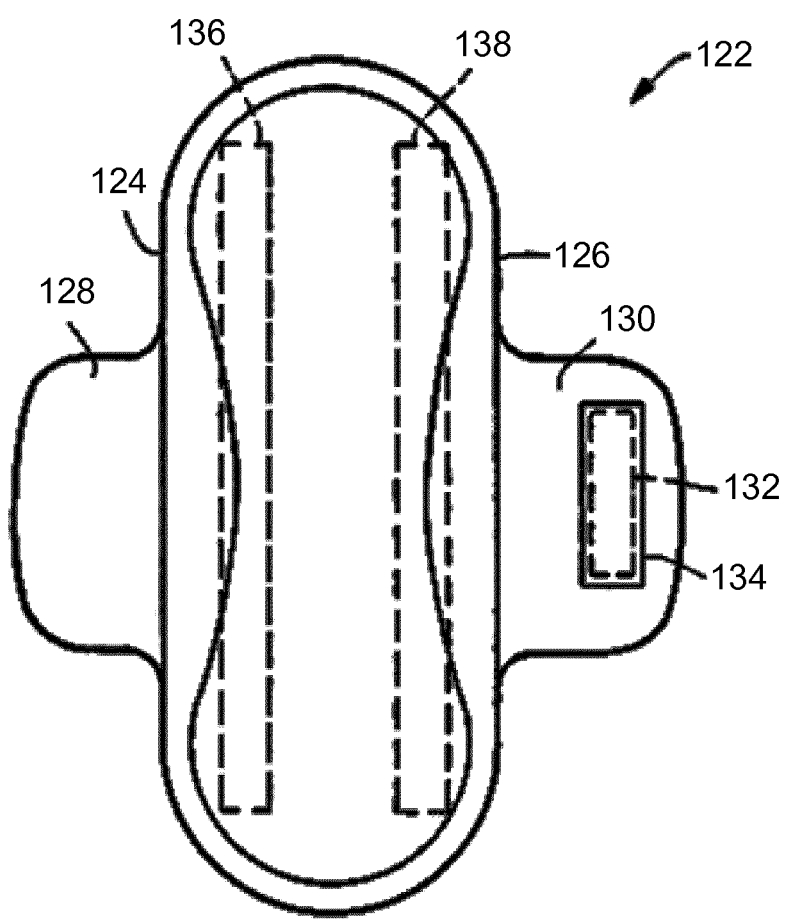
FIG. 1 is a schematic plan view of an absorbent article according to an aspect of the disclosure.
Figure 2A:
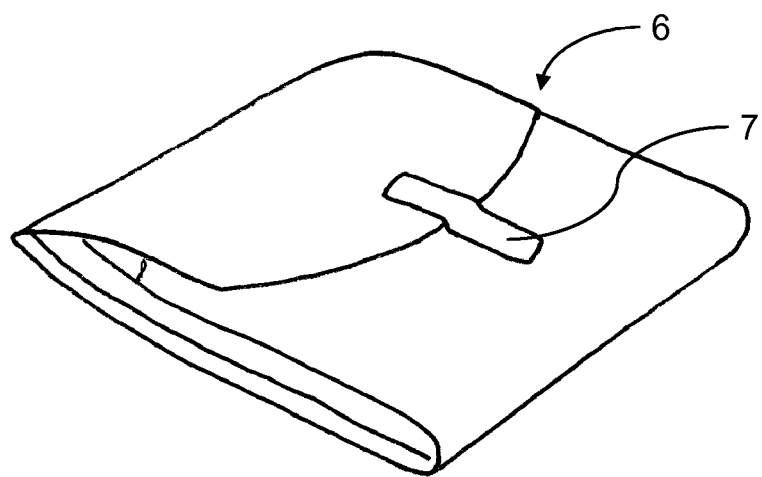
FIG. 2a-2b are schematic illustrations of a wrapped absorbent article according to an aspect of the disclosure.
Figure 2B:
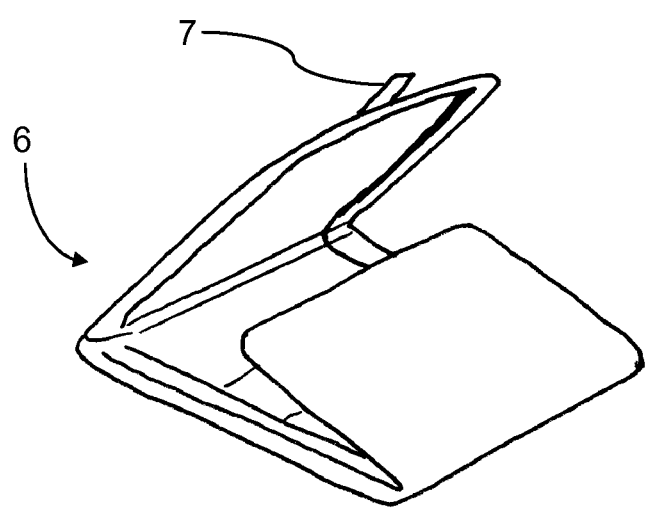
Figure 3:
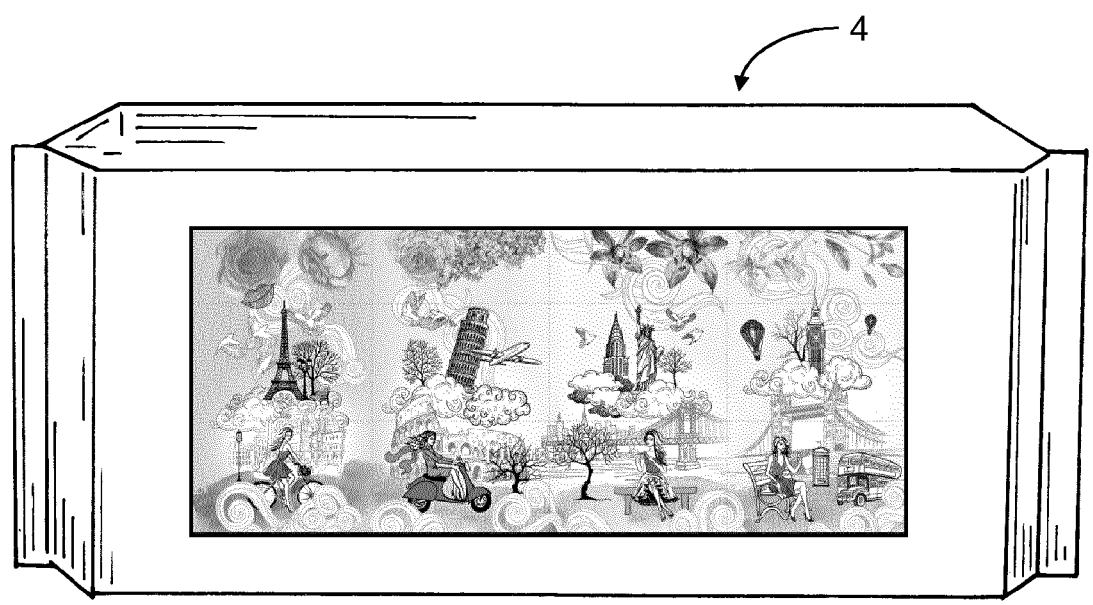
FIG. 3 is a schematic side view of a container according to an embodiment of the present disclosure.
Figure 4:
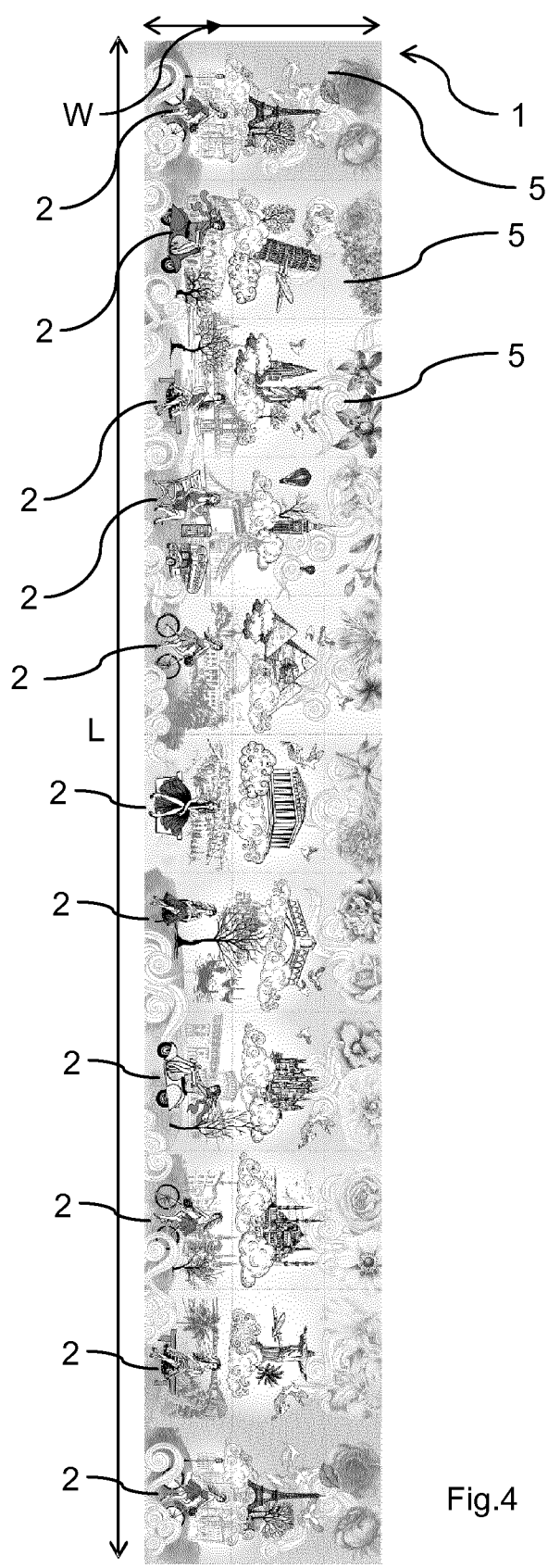
FIG. 4 is a schematic plan view of a single image according to an embodiment of the present disclosure.
Figure 5A:
FIG. 5a-5b are schematic illustrations of a pouch in unfolded and folded state according to an embodiment of the present disclosure.
Figure 5B:
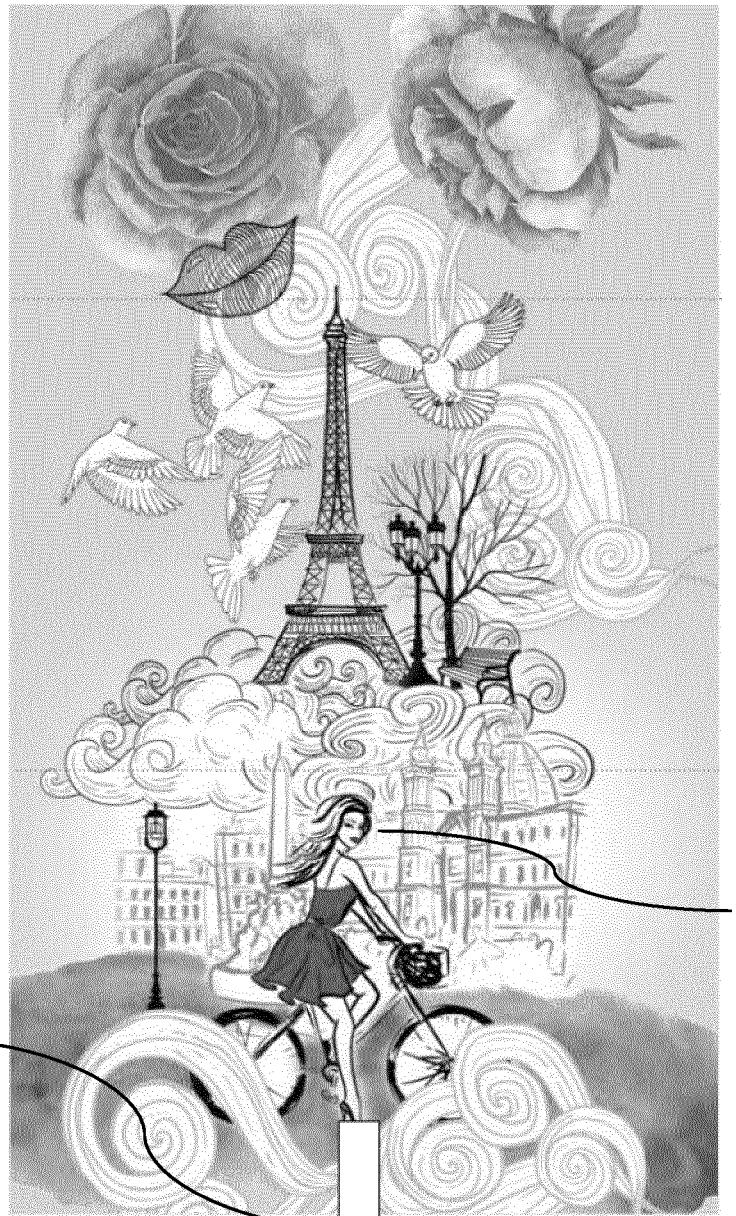

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. Herein, "comprise" and "include" mean that other elements and/or other steps which do not affect the end result can be added. Each of these terms encompasses the terms "consisting of" and "consisting essentially of".

"Centerline" as used herein means an imaginary line that is equidistant from lateral surfaces of the element referred to, typically running through said element such to divide said element into two substantially equal halves.

The expression "% by weight" (weight percent), here and throughout the description unless otherwise defined, refers to the relative weight of the respective component based on the overall weight of the formulation.

The recitation of numerical ranges by endpoints includes all numbers and fractions subsumed within that range, as well as the recited endpoints.

The expression "absorbent article" or "personal hygiene articles" or "personal hygiene absorbent articles" refers to articles which absorb and contain body exudates or discharges such as body fluids, and is intended to include sanitary napkins, pantiliners, diapers, and incontinence pads (and other articles worn in the crotch region of a garment).

The expression "disposable" refers to articles which are intended to be discarded after a single use, composted, or otherwise disposed of in an environmentally compatible manner. (That is, they are not intended to be laundered or otherwise restored or reused as an absorbent article.)

The expression "sanitary napkin" refers to articles which are worn by females adjacent to the pudendal region which are intended to absorb and contain the various exudates which are discharged from the body (e.g., blood, menses, and urine).

The expression "body surface" refers to surfaces of absorbent articles and/or their component members which face the body of the wearer, while the term "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

The expression "color system" refers to groups of colors which are different but similar one another. Preferred color systems include a blue color system, a pink color system, a orange color system, an yellow color system, and an green color system.

Figure 6:
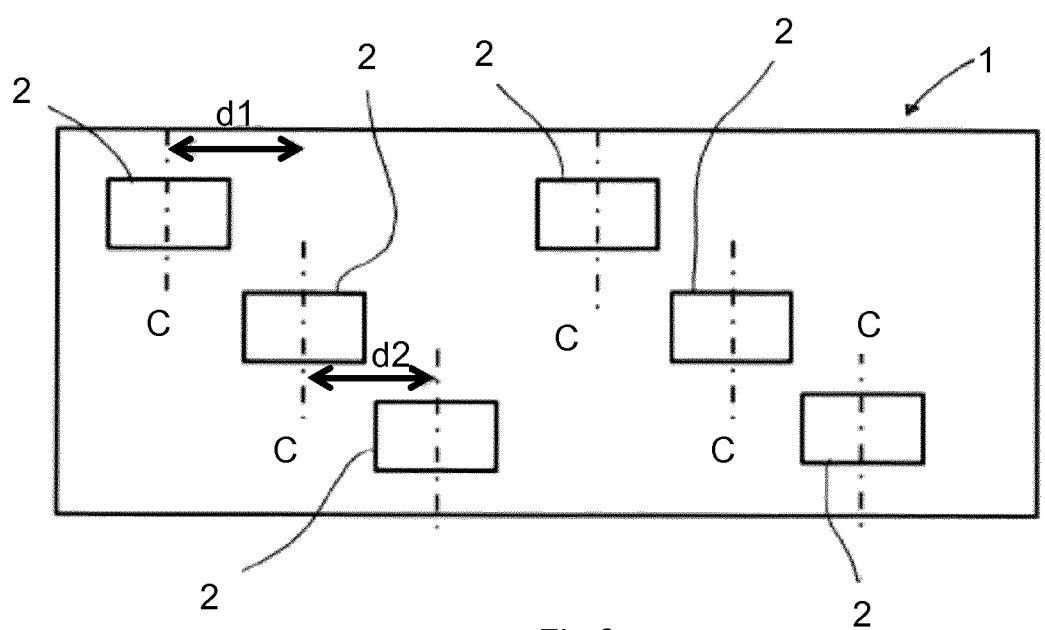
FIG. 6 is a schematic plan view of a single image according to an embodiment of the present disclosure.

The expression "skewed" refers to the condition where the centerline of each of at least two consecutive indicia do not overlap or are not aligned, preferably each said centerline being at a distance from each other as exemplified in FIG. 6.

The expression "graphic" refers to a pattern that is constituted by a motif(s) (i.e., a line(s)), a symbol(s), a color difference or transition of at least two colors, sceneries, and the like. The graphic preferably generates an aesthetic image and/or design that can provide emotional benefit(s) when the absorbent article having the graphic is looked or viewed by users.

The expression "indicia" refers to a visual marking(s) forming a distinctive element that may stand out from an image and/or graphic and is typically selected from the group consisting of an object (such as a hot-air balloon, a heart, a flower, a ball, a bicycle, a building and the like), a figure (such as a character selected from a man, a woman, a child, an animal, cartoon and the like), and combinations thereof.

The expression "demarcation" or "vertical demarcation" or "demarcation line" refers to solid lines within an image that are generally greater than 25% (preferably greater than 10%, more preferably greater than 5%, even more preferably greater than 2%, most preferably greater than 1%) of the width of the image, and that extend substantially parallel, preferably parallel, to the width of the image. By "substantially parallel" it is intended lines that are within an angle of ±10°, preferably ±5°, from an axis running parallel to the width of the image. Such may ensure that there are no divisions and/or breaks between consecutive images along a film/web of printed material and/or between sections of the same image, as described hereinbelow.

The expression "registered" refers to providing a control that permits an action to occur at a predetermined position. For example, in the case of registered cutting, this typically involves providing a mark within a printed body which when detected (e.g. via visual inspection by a camera) triggers a signal that activate a cutting means to provide a cut of the material at a predetermined position.

The expression "coloration treatment" refers to a treatment for making a color change in a material from its original color. In most cases, since component materials of the absorbent article typically have a white color, the coloration treatment changes the original white color to a non-white color (e.g., blue, red, yellow, green, gray, etc). Such a color change can be implemented by any technology known in the art. In one typical example, the coloration treatment is implemented by introducing or mixing a non-white color pigment(s) into the ingredient material(s) of an original material. In another typical example, the coloration treatment is implemented by printing an original material by a color ink(s). This coloration treatment by printing can be implemented by any conventional printing methods or technologies known in the art, including, but not limited to, a gravure printing, a flexography printing, a letter press printing, an offset printing, an ink jet printing, and the like, most preferably flexography printing.

Absorbent articles suitable for use herein are preferably female personal hygiene articles such as sanitary napkins, typically of the disposable type.

The Absorbent Article

FIG. 1 is a top plan view of a disposable absorbent article 122 (more particularly a sanitary napkin) which is one preferred embodiment of the present disclosure. The absorbent article typically comprises a liquid impermeable backsheet having a garment facing side and a body facing side opposite thereto, a liquid permeable topsheet positioned on the body facing side of the backsheet, and an absorbent core positioned between the backsheet and the topsheet. The absorbent core may comprise cellulosic fibers and/or super absorbent polymer particles, and may further comprise a nonwoven wrap that encloses said fibers and/or particles therein. A further optional intermediate layer may be comprised between the topsheet and the core, and can be selected from any nonwoven typically used in the art of acquisition and distribution layers, such as air-through-bonded nonwovens. The absorbent article 122 may further comprise opposed side edges 124, 126 extending substantially parallel to a longitudinal length of the absorbent article 122 that are typically perpendicular to a width of the absorbent article. Optionally, the absorbent article 122 may comprise one or more wings 128, 130 on at least a portion of each of the side edges 124, 126.

The absorbent article 122 may further comprise one or more first adhesive regions 136, 138 on the garment facing side of the backsheet that typically extend along the length of the absorbent article 122. Such first adhesive regions may be adapted to adhere to a wrap sheet arranged to form a pouch enclosing the absorbent article 122 and after removal of said wrap sheet adhere to a garment surface of the underwear of the wearer. Optionally, when the absorbent article comprises one or more wigs 128, 130, each said wing 128, 130 may comprise a second adhesive region 132 on the garment facing side and arranged to adhere to a garment surface of the wearer. In this embodiment, the absorbent article 122 comprises at least one protective strip 134 over the second adhesive region 132 to prevent it from adhering to the wrap sheet forming the pouch enclosing the absorbent article 122 when in the pre-use folded position (i.e. in the individually wrapped state prior to use/opening).

In an alternative embodiment (not shown), the absorbent article may be a tampon or a diaper (whether for babies or adult incontinence).

The Pouch

It should be noted that, in all embodiments disclosed herein, the absorbent article of the disclosure (e.g., a sanitary napkin) is wrapped by a wrapper sheet typically such that the absorbent article cannot be seen through the wrapper sheet. In an embodiment, the wrapper sheet has an opacity of greater than 50%, preferably greater than 60%, more preferably greater than 70%, most preferably from 75% to 100%, according to the method described herein.

The opacity of a sheet material shows the degree of un-clearness or un-transparency of the sheet material. When a sheet material has an opacity of 0%, the sheet material is completely transparent. On the other hand, if a sheet material has an opacity of 100%, the sheet material has no transparency, i.e., no light is transmitted through the material. The opacity of the wrapper sheet shows the degree on how clearly the absorbent article individually packaged by the wrapper sheet can be seen through the wrapper sheet.

The wrapper sheet (i.e. wrapping sheet) forming the pouch is generally printed on the outer surface thereof according to the process described herein. The print typically comprises not only colors but also indicia and/or elements forming a scene and/or providing a portion of a story.

An aspect of the disclosure is directed to, an array of pouches comprising a wrapping sheet 3 each for containing a single personal hygiene absorbent article therein, each said pouch 6 comprising an interior surface facing the personal hygiene absorbent article and an external surface opposite thereto, the external surface comprising printed indicia 2 arranged such that when a plurality of said pouches in the container are stacked side-by-side they form at least one single substantially harmonious image 1.

In a preferred embodiment, the substantially harmonious image 1 is arranged to provide a story and/or theme that provides a visual sensory trigger to the comfort, performance and/or intended use of said personal hygiene absorbent articles.

Preferably any one pouch within the array of pouches is different from at least each neighboring pouch, preferably wherein said pouches have a different graphic (5) but at least one common indicia (2).

In yet another preferred embodiment, the garment surface of the absorbent article has a first coloration treatment, while the wrapper sheet has a second coloration treatment.

In an embodiment, the first and second coloration treatments produce first and second primary colors which are selected from one color system. More specifically, in preferred embodiments, the garment surface of the absorbent article and the wrapper sheet have first and second coloration treatments producing first and second primary colors, respectively, which are selected from a color system which is selected from the group consisting of a blue color system, a pink color system, a green color system, an orange color system, and an yellow color system.

The wrapper sheet is preferably manufactured from a thin flexible material. The wrapper sheet material is preferably liquid impermeable so that the wrapper sheet will be suitable for wrapping and disposing of a used sanitary napkin. In preferred embodiments, the wrapper sheet is the form of a film or a nonwoven web or a film laminated with a nonwoven web.

Preferred materials for the wrapper sheet of the present disclosure typically include a thermoplastic polymer, a pigment and a filler (inorganic or organic). Typically, the materials for the pigment and filler are in the form of a particle. Such particles are dispersed in the thermoplastic polymer. Preferably, pigments or fillers are contained no more than about 20% of a film. (If desired, the particles of the pigment or the filler can be coated with a fatty acid ester to obtain higher loadings in the polymer.) In preferred embodiments, the optical properties of the wrapper sheet, i.e., the opacity Suitable thermoplastic polymers include polyolefin such as polyethylene (PE), including a liner low density polyethylene (LLDPE), a low density polyethylene (LDPE), a ultra low density polyethylene (ULDPE), a high density polyethylene (HDPE), a polypropylene, and a mixture thereof. Other suitable thermoplastic polymers which may also be used include, but are not limited to a polyester, a polyurethane, a compostable or biodegradable polymer, a thermoplastic elastomer, and a metallocene catalyst-based polymer. Preferably, the material for the filler is an inorganic material which is selected from the group consisting of a titanium dioxide, a zinc oxide, a calcium carbonate, a mica and a mixture thereof. Alternatively (or if desired), the material for the filler can be an organic material such as a high-density polyethylene or other organic polymer material such as a polypropylene.

In a manufacture process, the thermoplastic polymer, filler and pigment are mixed or blended together to form a homogeneous mixture in a suitable mixing extrude, or in a separate preliminary compounding step. The mixture is then cast or blown into a film or nonwoven web.

In alternative preferred embodiments, the optical properties of the wrapper sheet can be also controlled by changing the kinds and amount of ingredients of the ink(s) to be used for printing the surface of the wrapper sheet material.

Printing of indicia and/or graphics over the wrapper sheet(s) can be done by any conventional printing methods know in the art such as a gravure printing, a flexography printing, a letter press printing, an offset printing, an ink jet printing, and the like, most preferably by flexography printing typically using the CMYK (cyan, magenta, yellow and key (i.e. black)) color model. Typically, a printing ink contains about 20-60% of a binder resin or filler, about 40-60% of a pigment (or dye), and additives such as process aid(s) which are typically used for drying up the solvents after the printing process.

The amount of the filler affects the opacity level of the wrapper sheet. For example, increasing the filler material makes the resultant material more translucent, while decreasing the filler material makes the resultant material more transparent. Thus, in preferred embodiments, the opacity level of the wrapper sheet is controlled by changing the amount fillers contained in the wrapper sheet material.

The opacity level of the wrapper sheet can also be controlled by the kinds and amount of ingredients of the ink(s) to be used for printing the surface of the wrapper sheet material. In order to increase the opacity level, an ink which contains an inorganic pigment(s) such as a titanium dioxide, a zinc oxide, a calcium carbonate, and the like is preferably used. Such inorganic pigment(s) can provide higher opacity by increasing its amount. The particle size of the inorganic pigment(s) can vary depending on the printing method to be employed. In a preferred embodiment, a titanium dioxide is preferably used as the pigment.

In an embodiment, the wrapper sheet has a coloration treatment which produce a primary color by tinting, i.e., adding a pigment(s) into the film ingredients. The pigment(s) should be selected depending on the target coloration treatment. An appropriate selection of a pigment(s) contributes to a production of a wrapper sheet having an expected non-white color (e.g., blue, red, yellow, green, gray, etc).

In an alternative embodiment, the wrapper sheet has a coloration treatment which produce a primary color by printing over a colored or substantially non-colored wrapper sheet.

The wrapper sheet having a coloration treatment can also be produced by changing the kinds and amount of ingredients of the ink(s) to be used for printing the surface of the wrapper sheet material.

The sanitary napkin 122 of the disclosure is wrapped by the wrapper sheet 3. In one embodiment, a folded (or un-folded if desired) sanitary napkin is put in a pouch formed by said wrapper sheet. Such a pouch is typically formed by folding and sealing the edges of a wrapper sheet.

Preferably, the wrapper sheet and the sanitary napkin are folded together around two fold lines (if desired the number can be one or three) to provide an individually packaged structure for the sanitary napkin.

In a preferred embodiment each pouch (or wrap/wrapper/wrapping) comprises a re-sealable fastener 7 arranged to keep the pouch in a closed state and/or to enable the pouch to be re-closed with a used product for disposal thereof.

Preferably, individually packaged sanitary napkins each wrapped by a wrapper sheet are stacked, compressed and contained in a package (i.e. container) such as a bag of polymeric film or cardboard box.

The Container

According to the disclosure, the container 4 comprises a plurality of individually wrapped personal hygiene absorbent articles, wherein each personal hygiene absorbent article is wrapped within a pouch formed by a printed wrapping sheet 3, each pouch comprising an interior surface facing the personal hygiene absorbent article and an external surface opposite thereto, the external surface comprising printed indicia 2 thereon, and arranged such that when a plurality of said pouches within the container are stacked side-by-side they form at least one single substantially harmonious image 1, and wherein at least a portion of said pouches are viewable through said container 4.

In a preferred embodiment, the container consists of a transparent bag, preferably comprising one or more printed areas having one or more colors resulting in an opacity of greater than 50%, preferably greater than 60% and at least one non-printed area having an opacity of less than 25%. Preferably at least one of the colors is substantially the same as one of the colors present on each of the individually wrapped articles (or pouches).

In an alternative embodiment, the container consists of a cardboard box comprising a substantially transparent or translucent window through which at least a portion of the individually wrapped articles can be seen through from the outside of said container.

Preferably any one pouch within the container is different from at least each neighboring pouch in an array of pouches, preferably wherein said pouches have a different graphic but at least one common indicia.

The Process of Making

According to the disclosure, the process for making individually wrapped personal hygiene absorbent articles comprises the steps of:

(i) providing a single image 1 having a width (W) and a length (L) and comprising one or more, preferably a plurality of, indicia 2 wherein at least one of the indicia 2 is repeated more than once within said single image 1;

(ii) printing a plurality of said single images over a continuous film and/or web of material to form a continuous repetition of the same single image in a side-by-side arrangement with the length (L) of the image extending along a length of the continuous film and/or web of material and the width (W) of the image corresponding to the width of said continuous film and/or web of material;

(iii) cutting the printed film and/or web material along a transverse axis perpendicular to said length (L) such to form a plurality of individual segments of film and/or web material forming individual wrapping sheets 3 comprising a portion of said single image 1 and sized such to each accommodate one of said personal hygiene absorbent articles therein;

(iv) wrapping individual personal hygiene absorbent articles each with one of said wrapping sheets 3 such that a printed portion of the wrapping sheet 3 is viewable;

(v) stacking a plurality of the individually wrapped personal hygiene absorbent articles into a container 4;

wherein said image is free of demarcation lines extending perpendicular to the length (L) and parallel to the width (W) of said image, and wherein said stacked plurality of individually wrapped personal hygiene absorbent articles when unwrapped and/or positioned side by side substantially reconstruct said single image 1, and wherein the cutting step is not registered. It has been found that creating images and sceneries free of demarcation lines allow for a cutting step that does not require controlling a predetermined position of cutting (e.g. via a registered cutting step) thus considerably simplifying the process, this in turn ensures that when individual wrappings are stacked they still re-create the original image without the risk of vertical lines being present that would distract and/or break the continuous story.

In an embodiment, the wrapping sheet of each of the stacked plurality of the individually wrapped personal hygiene absorbent articles within the container have a common theme.

In an embodiment, each of the wrapping sheets 3 of the plurality of the individually wrapped personal hygiene absorbent articles stacked within the container 4 provide a portion of a story that progresses from one wrapping sheet 3 to the next typically starting from a first wrapping sheet 3 proximal to an opening of said container 4 to a last wrapping sheet 3 distal from said opening, preferably wherein said story in its entirety is contained within said single image 1. Without wishing to be bound by theory it is further believed that creating such an additional sensory experience to particularly hygiene articles of the sanitary napkin type, distracts users from the melancholic mood during the menstruation period and rather further create an improved perception of performance and attention to detail, as well as curiosity and interaction with the product that may be particularly beneficial for teenagers who start using such products for the first time.

In an embodiment, the printing step comprises printing said images with at least four colors, preferably more than four colors (preferably more than five, more preferably more than six, even more preferably at least eight) but generated from the CMYK (cyan, magenta, yellow and key (i.e. black)) color model.

In an embodiment, the printing step comprises printing four overlaid sub-images each from one of the colors selected from cyan, magenta, yellow and black to generate the single image. This has the advantage of allowing a plurality of colors (four or more) to be printed onto the pouches in a quick and effective process that can be implemented in both an in-line or batch process.

In an embodiment, at least one of the indicia 2 is comprised on the wrapping of each of said plurality of stacked individually wrapped personal hygiene absorbent articles. This has the advantage of ensuring a coherent theme is carried through between pouches within a container.

In an embodiment, the wrapping sheets 3 form individual pouches containing the absorbent article therein, the pouches being stacked such that any one pouch within the container is different from at least each neighboring pouch in an array of pouches, preferably wherein said pouches have a different graphic but at least one common indicia. This may help in ensuring a coherent theme is carried through between pouches within a container.

In a preferred embodiment, the plurality of indicia of the image are skewed along an axis parallel to the width (W), preferably wherein each indicia 2 has a centerline C and each said centerline being separated by a distance (d1, d2) along said axis. In an embodiment each distance (d1, d2) is substantially equal, in an alternative embodiment each distance (d1, d2) is different. An advantage of such arrangement is that it enables having a cutting process step that does not need to be registered and still ensure that each pouch generated comprises at least one full indicia. Such also has the advantage of reducing the process complexity and cost.

Preferably, the distance (d1, d2) is greater than 0 mm. Most preferably the distance (d1, d2) is greater or equal to a second distance separating a cutting and a sealing station and/or the distance (d1, d2) is from 90 mm to 150 mm, preferably from 95 mm to 140 mm, more preferably from 110 mm to 130 mm.

Test Methods

Opacity:

A dispersion colorimeter is preferably used for determining the opacity of a sample material. A preferred dispersion colorimeter is available from BYK-Gardner GmbH, Geretsried, Germany, under Trade Name "BYK Gardner Color-Guide 45/0" (Cat. No. 6800).

The measurements should be conducted by using a light source "A" at a viewing angle of 2° (degrees). This dispersion colorimeter includes a light source for Illuminant A (i.e., an approximation of incandescent lamp having a correlated color temperature of about 3000 K), a flat table, a white standard plate, a standard black plate, a photo detector which includes a multi-celled photo-detector diode array, and a computer. The white and black standard plates are available from the same company under Cat. Nos. 6811 and 6810, respectively. In the measurement, the white standard plate is placed on the flat table. A sample material is put on the white standard plate in a flat state. The sample material is illuminated by the light source with an incident angle of 45°. The reflection light which is reflected from the sample material is received by the photo detector with a receiving angle of 0°. The reflection rate (Yw) of the reflection light is detected by the photo detector. Similarly, after the black standard plate is placed on the flat table, the sample material is put on the black standard plate in a flat state. The sample material is illuminated by the light source with an incident angle of 45°. The reflection light which is reflected from the sample material is received by the photo detector with a receiving angle of 0°. The reflection rate (Yb) of the reflection light is detected by the photo detector. The opacity (OP) is obtained by the following formula:

$$OP (\%) = (Yb/Yw) \times 100 \qquad (1)$$

This process is repeated for one sample sheet material at least five times and the average value of the opacities (OP) measured is calculated and recorded by the colorimeter. The average value of the opacities measured is called the opacity of a sheet material.

It is supposed that the present invention is not restricted to any form of realization described previously and that some modifications can be added to the presented example of fabrication without reappraisal of the appended claims.

The invention claimed is:

1. A process for making individually wrapped personal hygiene absorbent articles comprising the steps of:
   (i) providing a single image (1) having a width (W) and a length (L) and comprising a plurality of indicia (2) wherein at least one of the indicia (2) is repeated more than once within said single image (1), wherein the plurality of indicia (2) are skewed along an axis parallel to the width (W), wherein each indicia has a centerline (C) and each said centerline (C) is separated by a distance (d1, d2) along said axis, and wherein the distance (d1, d2) is greater or equal to a second distance separating a cutting and a sealing station and/or wherein the distance (d1, d2) is from 90 mm to 150 mm;
   (ii) printing said single image, over a continuous film and/or web of material with the length (L) of the image extending along a length of the continuous film and/or web of material and the width (W) of the image corresponding to the width of said continuous film and/or web of material;
   (iii) cutting the printed film and/or web material along a transverse axis perpendicular to said length (L) such to form a plurality of individual segments of film and/or web material forming individual wrapping sheets (3) comprising a portion of said single image (1) and sized such to each accommodate one of said personal hygiene absorbent articles therein;
   (iv) wrapping individual personal hygiene absorbent articles each with one of said wrapping sheets (3) such that a printed portion of the wrapping sheet (3) is viewable;
   (v) stacking a plurality of the individually wrapped personal hygiene absorbent articles into a container (4);
   wherein said image is free of demarcation lines extending perpendicular to the length (L) and parallel to the width (W) of said image, and wherein said stacked plurality of individually wrapped personal hygiene absorbent articles when unwrapped and/or positioned side by side substantially reconstruct said single image (1), and wherein the cutting step is not registered.

2. A process according to claim 1 wherein the wrapping sheet (3) of each of the stacked plurality of the individually wrapped personal hygiene absorbent articles within the container have a common theme.

3. A process according to claim 1 wherein each of the wrapping sheets (3) of the plurality of the individually wrapped personal hygiene absorbent articles stacked within the container (4) provide a portion of a story that progresses from one wrapping sheet (3) to the next starting from a first wrapping sheet (3) proximal to an opening of said container (4) to a last wrapping sheet (3) distal from said opening.

4. The process according to claim 3, wherein said story is contained within said single image (1).

5. A process according to claim 1 wherein the printing step comprises printing said images with at least four colors.

6. A process according to claim 1 wherein at least one of the indicia (2) is comprised on the wrapping of each of said plurality of stacked individually wrapped personal hygiene absorbent articles.

7. A process according to claim 1 wherein the wrapping sheets (3) form individual pouches containing the absorbent article therein, the pouches being stacked such that any one pouch within the container is different from at least each neighboring pouch in an array of pouches.

8. The process according to claim 7, wherein said pouches have a different graphic but at least one common indicia.

9. The process according to claim 1, wherein the distance (d1, d2) is greater or equal to a second distance separating a cutting and a sealing station and/or wherein the distance (d1, d2) is from 95 mm to 140 mm.

10. The process according to claim 1, wherein the distance (d1, d2) is greater or equal to a second distance separating a cutting and a sealing station and/or wherein the distance (d1, d2) is from 110 mm to 130 mm.

11. A container comprising a plurality of individually wrapped personal hygiene absorbent articles obtained by a process comprising the steps of:
   (i) providing a single image (1) having a width (W) and a length (L) and comprising a plurality of indicia (2) wherein at least one of the indicia (2) is repeated more than once within said single image (1), wherein the plurality of indicia (2) are skewed along an axis parallel to the width (W), wherein each indicia has a centerline (C) and each said centerline (C) is separated by a distance (d1, d2) along said axis, and wherein the distance (d1, d2) is greater or equal to a second distance separating a cutting and a sealing station and/or wherein the distance (d1, d2) is from 90 mm to 150 mm;

(ii) printing said single image, over a continuous film and/or web of material with the length (L) of the image extending along a length of the continuous film and/or web of material and the width (W) of the image corresponding to the width of said continuous film and/or web of material;

(iii) cutting the printed film and/or web material along a transverse axis perpendicular to said length (L) such to form a plurality of individual segments of film and/or web material forming individual wrapping sheets (3) comprising a portion of said single image (1) and sized such to each accommodate one of said personal hygiene absorbent articles therein;

(iv) wrapping individual personal hygiene absorbent articles each with one of said wrapping sheets (3) such that a printed portion of the wrapping sheet (3) is viewable;

(v) stacking a plurality of the individually wrapped personal hygiene absorbent articles into a container (4);

wherein said image is free of demarcation lines extending perpendicular to the length (L) and parallel to the width (W) of said image, and wherein said stacked plurality of individually wrapped personal hygiene absorbent articles when unwrapped and/or positioned side by side substantially reconstruct said single image (1), and wherein the cutting step is not registered.

\* \* \* \* \*